United States Patent
Mengel et al.

(10) Patent No.: US 7,924,436 B2
(45) Date of Patent: Apr. 12, 2011

(54) METHOD FOR APPROXIMATING AN INFLUENCE OF AN OPTICAL SYSTEM ON THE STATE OF POLARIZATION OF OPTICAL RADIATION

(75) Inventors: Markus Mengel, Heidenheim (DE); Michael Totzeck, Schwaebish Gmuend (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 943 days.

(21) Appl. No.: 11/703,570

(22) Filed: Feb. 7, 2007

(65) Prior Publication Data

US 2007/0182969 A1    Aug. 9, 2007

Related U.S. Application Data

(60) Provisional application No. 60/771,395, filed on Feb. 8, 2006.

(51) Int. Cl.
*G01B 11/02* (2006.01)
*G01B 9/02* (2006.01)

(52) U.S. Cl. ...................... 356/515; 356/495

(58) Field of Classification Search ............ 356/491, 356/492, 495, 515, 520
See application file for complete search history.

(56) References Cited

U.S. PATENT DOCUMENTS

| | | | |
|---|---|---|---|
| 5,298,972 A | 3/1994 | Heffner | |
| 7,277,182 B2 * | 10/2007 | Wegmann et al. | 356/494 |
| 2002/0024673 A1 | 2/2002 | Ouchi | |
| 2004/0114150 A1 | 6/2004 | Wegmann et al. | |
| 2004/0262500 A1 | 12/2004 | Mengel | |

FOREIGN PATENT DOCUMENTS

| | | |
|---|---|---|
| DE | 103 04 822 A1 | 1/2003 |
| EP | 1369662 A2 | 12/2003 |

OTHER PUBLICATIONS

Xie, Xiaoliang et al. "Picosecond circular dichroism spectroscopy: a Jones matrix analysis". J. Opt. Soc. Am. B, vol. 7, No. 8, Aug. 1990, pp. 1673-1864.*

* cited by examiner

*Primary Examiner* — Michael A Lyons
(74) *Attorney, Agent, or Firm* — Sughrue Mion, PLLC

(57) ABSTRACT

A method for approximating an influence of an optical system on the state of polarization of optical radiation comprises the steps of providing incoming optical radiation for the optical system in several incoming states of polarization, including at least one incoming state having circularly polarized radiation components; directing the incoming optical radiation onto the optical system; measuring at least one characteristic, including a phase distribution, of a resulting outgoing optical radiation emerging from the optical system with respect to each of the incoming states of polarization; and approximating the influence of the optical system on the state of polarization of optical radiation by evaluating the measured characteristics of the outgoing optical radiation.

29 Claims, 2 Drawing Sheets

METHOD FOR APPROXIMATING AN INFLUENCE OF AN OPTICAL SYSTEM ON THE STATE OF POLARIZATION OF OPTICAL RADIATION

CROSS REFERENCE TO RELATED APPLICATION

This application claims benefit of priority from U.S. Provisional Application Ser. No. 60/771,395, filed Feb. 8, 2006, entitled "METHOD FOR APPROXIMATING AN INFLUENCE OF AN OPTICAL SYSTEM ON THE STATE OF POLARIZATION OF OPTICAL RADIATION".

BACKGROUND OF THE INVENTION

1. Field of the Invention

The invention relates to a method for approximating an influence of an optical system on the state of polarisation of optical radiation. Such a method can e.g. be applied to microlithographic systems. The term "optical system" is to be understood as any arrangement of one or more optical components which transmit and/or reflect incident optical radiation, in particular including lenses and objectives constructed therewith. In the case of a microlithographic system the optical system can e.g. be the projection objective of such a system. The term "optical radiation" is to be understood as any desired electromagnetic radiation which is applied to the optical system under test, for example visible light or UV radiation. In order to describe the state of polarisation and how it is influenced or changed by the optical system, use is generally made of suitable variables such as the Stokes parameters, the Muller matrix, the Polarisation matrix and the Jones matrix. Reference may be made to the relevant literature for details in this regard.

2. Description of the Related Art

A method for determining an influence of an optical system on the state of polarisation of optical radiation is described in the German patent application 103 04 822 A1. With this method a Jones matrix of the optical system is determined in two measurement stages. In the first stage entrance-side radiation of defined polarisation states is directed onto the optical system. The intensities of the resulting exit states of polarisation of the radiation emerging from the optical system is then measured using a polarisation analyser. From this measurement data a phase-reduced Jones matrix is calculated. In a second measurement stage a global pupil resolved phase term is determined by an interferometric measurement. In this measurement one single entrance-side polarisation state is used for determining the global phase term of the resulting radiation emerging from the optical system. The phase-reduced Jones matrix determined in the first measurement stage and the global phase term is then combined in order to obtain the complete Jones matrix of the optical system.

In the patent application U.S. 2002/0024673 A1 a wave front measuring device is described for obtaining information on the influence of an optical system on the state of polarisation of optical radiation. This wave front measuring device contains an entrance-side polariser for generating at least two different linearly polarised states, an interferometer of the Twyman-Green or Fizeau type for measuring a wave front. Further, the wave front measuring device includes a detector-side polariser, which is required to analyze the polarisation state of the light emanating from the optical system.

SUMMARY OF THE INVENTION

It is an object of the present invention to provide a method of the above mentioned type, which allows an approximation of an influence of an optical system on the state of polarisation of optical radiation with less cost and improved accuracy.

In order to solve the above object, according to the present invention a method for approximating an influence of an optical system on the state of polarisation of optical radiation is provided, which comprises the steps of providing incoming optical radiation for the optical system in several incoming states of polarisation, including at least one incoming state having circularly polarised radiation components; directing the incoming optical radiation onto the optical system, measuring at least one characteristic, including a phase distribution, of a resulting outgoing optical radiation emerging from the optical system with respect to each of the incoming states of polarisation; and approximating an influence of the optical system on the states of polarisation of optical radiation by evaluating the measured characteristics of the outgoing optical radiation.

According to the invention the influence of an optical system on the state of polarisation of optical radiation can be approximated without having to use a polariser for analysing the outgoing optical radiation, which is of particular interest in the case of an optical system which has a large numerical aperture on the output side. Instead, the phase distribution of the resulting outgoing optical radiation is measured using appropriate means without the need of a polariser on the detector-side. Therefore, the cost of manufacturing a polariser for the detector side, which is generally subject to tight requirements due the need of providing sufficient transmission and extinction for a large angle can be avoided. In particular for the UV-wavelengths of $\lambda=193$ nm and $\lambda=248$ nm polarisers of sufficient quality for use as a detector-side polarizer in an apparatus according to the prior art cannot be manufactured in a sufficient quality. This is particularly true in the case, in which a high aperture divergent beam is generated in a shearing interferometer. By providing the method according to the present invention, which does not require a detector-side polariser, the measurement errors introduced by such a polariser can be avoided, and therefore the influence of the optical system on the state of polarisation can be approximated with an improved accuracy. The method according to the present invention is particularly suited for optical radiation at a wavelength of 193 nm or 248 nm.

The above object is further solved according to the present invention by providing a method for approximating an influence of an optical system on the state of polarisation of optical radiation comprising the steps of providing incoming optical radiation for the optical system in several incoming states of polarisation; directing the incoming optical radiation onto the optical system; measuring at least one characteristic of a resulting outgoing optical radiation emerging from the optical system with respect to each of the incoming states of polarisation; and approximating the influence of the optical system on the state of polarisation of optical radiation by calculating the rotation and/or the circular dichroism of the optical system from the measured characteristics of the outgoing optical radiation. By calculating the rotation and/or the circular dichroism the influence of the optical system on the state of polarisation of optical radiation can be approximated to a high accuracy without the requirement of a polariser for measuring the outgoing optical radiation on the detector-side.

The above-mentioned object is further solved according to the invention by providing a method for approximating an influence of an optical system on the state of polarisation of optical radiation, which comprises the steps of providing incoming optical radiation for the optical system in several incoming states of polarisation; directing the incoming optical radiation onto the optical system; measuring at least one characteristic, including a phase distribution, of a resulting outgoing optical radiation emerging from the optical system with respect to each of the incoming states of polarisation using a common path interferometer, which causes interference of at least two partial optical waves travelling on a common path in said interferometer, and approximating the influence of the optical system on the state of polarisation of optical radiation by evaluating the measured characteristics of the outgoing optical radiation.

By measuring the phase distribution for each of the incoming states of polarisation using a common path interferometer the influence of an optical system on the state of polarisation can be approximated with a very high accuracy without the need of using a polariser for measuring the resulting outgoing optical radiation. The term "common path interferometer" is to be understood in this case as an interferometer, in which the at least two partial optical waves interfering with each other travel on essentially a common path. Preferably the two partial waves travel on the same path in the interferometer, while the two partial waves travel on a similar, but not identical path inside the optical system under test. This is in contrast to for example a Twyman-Green or a Fizeau Interferometer, in which a reference beam is routed on a different path than a measurement beam it is interfering with and which traverses the optical system under test. Examples of a common path interferometer include a shearing interferometer and a point diffraction interferometer. When measuring a phase distribution with a common path interferometer, the aberrations of the detection optics do not directly influence the phase measurements, therefore the influence of an optical system on the state of polarisation can be approximated with a high accuracy. The two partial optical waves travelling on a common path of the common path interferometer, according to the invention advantageously both contain optical radiation having passed through the optical system. It is further feasible, if the several incoming states of polarisation of the incoming optical radiation are provided to the optical system one after the other, so that the measured characteristics of resulting outgoing optical radiation can be easily attributed to the respective incoming states.

Further, the above object is solved according to the invention by providing a method for approximating an influence of an optical system on the state of polarisation of optical radiation comprising the steps of providing incoming optical radiation for the optical system in at least one incoming state of polarisation; directing the incoming optical radiation onto the optical system; measuring at least one characteristic of a resulting outgoing optical radiation emerging from the optical system with respect to each of the at least one incoming state of polarisation without the use of a polariser; and approximating the influence of the optical system on the state of polarisation of optical radiation from the measured at least one characteristic of the outgoing optical radiation.

In a development of the method according to the present invention the measuring of the at least one characteristic of the outgoing optical radiation includes measuring a phase distribution and/or an intensity distribution of the outgoing optical radiation with respect to each of the incoming states of polarisation. The term "phase distribution" and the term "intensity distribution" is to be understood as the respective distribution over at least portions of the exit pupil of the optical system. From the phase distribution and/or the intensity distribution for each of the incoming states of polarisation the influence of the optical system on the state of polarisation can be approximated with a particularly high accuracy.

It is further feasible, if the measuring of a phase distribution and/or an intensity distribution includes the use of an interferometer, in particular a common path interferometer like a shearing interferometer and/or a point diffraction interferometer. As detailed above, the use of a common path interferometer allows minimizing the influence of aberrations of the detection optics on the measurement. In particular it is advantageous, if the interferometer employed in the method according to the invention allows the use of the same radiation as is used in an actual lithographic operation of the optical system. This measurement technology is also denoted as operational interferometer (OI) measurement technology.

In a further development of the method according to the invention the approximating of the influence of the optical system on the state of polarisation of optical radiation includes processing the measured phase distributions and/or the measured intensity distributions in a model function. Further, the approximating of the influence of the optical system on the state of polarisation of optical radiation advantageously includes a reconstruction of an approximated Jones matrix of the optical system. Therewith, the influence of an optical system on the state of polarisation can be determined with a particularly high accuracy. In particular the Jones matrix can therewith be determined with a maximum relative error of all matrix elements of less than 0.05.

It is further advantageous, if the incoming states of polarisation are selected such, that any arbitrary state of polarisation can be formed by a linear combination of the incoming states of polarisation. In particular any polarised state and any circularly or elliptically polarised state can be formed by linear combination of the incoming states of polarisation.

In a further advantageous aspect of the invention the optical system comprises an optical imaging system having a given aperture, and the influence of the optical system on the state of polarisation of optical radiation is determined with pupil resolution. That means, the influence of the optical system is determined over the respective angles of the exit pupil. For this purpose, it is particularly advantageous, if the measured phase distribution and/or the measured intensity distribution detailed above is each a distribution over the whole exit pupil. It is particularly advantageous if the optical imaging system has a high numerical aperture of at least 0.8.

It is further advantageous, if the incoming radiation is provided in at least one first incoming state having predominantly linearly polarised radiation components and at least one second incoming state having predominantly circularly polarised radiation components. The at least one first incoming state having predominantly linearly polarised radiation components allows the determination of so-called linear characteristics of the optical system, like the retardation, the transmission and the linear dichroism. Providing at least one second incoming state having predominantly circularly polarised radiation components allows the determination of the rotation and the circular dichroism of the optical system. From these parameters the influence of the optical system on the state of polarisation can be approximated with a very high precision.

In a further development of the invention a predominant polarisation direction of the linearly polarised radiation components of the at least one first incoming state is varied between at least three polarisation directions obtained by rotating the azimuth angle $\phi$ of the predominant polarisation direction in the range of $0° \leq \phi < 180°$ in equal steps. An incoming state having a polarisation direction of an azimuth angle $\phi$ in the range of $0° \leq \phi < 360°$ always has an equivalent incoming state having a polarisation direction of an azimuth angle in the range of $0° \leq \phi < 180°$ mentioned above due to the symmetry of the electrical field with respect to the propagation axis. That means, e.g. an incoming state having an azimuth angle of 180° is equivalent to an incoming state having an azimuth angle of 0° and is therefore already covered by referring to the incoming state having an azimuth angle of 0°.

In the above development of the invention at least three first incoming states are provided, for example the predominant polarisation direction is subsequently adjusted to the azimuth angles of 0°, 60° and 120° or the azimuth angles of 30°, 60° and 90°, etc. The angular step between the polarisation directions can certainly be selected to be smaller. It is further feasible if a variation in a phase distribution and an intensity distribution of the measured outgoing optical radiation resulting from the variation of the predominant polarisation direction is measured, and the retardation and the linear dichroism of the optical system are determined therefrom. The orientation of the main axes of both the retardation and the linear dichroism is advantageously determined therefrom further. By rotating the predominant polarisation direction in the above-mentioned way the retardation and the linear dichroism of the optical system can be determined with a high degree of accuracy and therefore the influence of the optical system can be approximated particularly precisely. According to the method of the present invention the retardation can be determined with an pupil averaged error of less than 1.67 nm. Further, the pupil averaged error of the linear dichroism can be held below 0.005.

In a further development of the method according to the invention the at least one second incoming state comprises a first incoming circular polarisation state of predominantly left-handed circularly polarised light and a second incoming circular polarisation state of predominantly right-handed circularly polarised light. It is further advantageous, if the rotation and the circular dichroism of the optical system are determined from the outgoing optical radiation relating to the first and the second incoming circular polarisation state. According to the method of the present invention the rotation can be determined with a pupil averaged error of less than 0.14°. This allows the reconstruction of an approximated Jones matrix with a high degree of accuracy.

In an advantageous embodiment the transmission of the optical system is determined from the measured characteristics of the outgoing optical radiation relating to the at least one first incoming state of polarisation and/or the at least one second incoming state of polarisation. This allows the reconstruction of a Jones matrix of the optical system with high accuracy.

In a further development of the invention the incoming states of polarisation are provided by varying the polarisation state of the incoming optical radiation by means of at least one combination of a polariser and a retarder, each of the at least one polariser and the at least one retarder being independently adjustable in its respective spatial orientation. Therewith a broad range of incoming states of polarisation can be generated, in particular linearly polarised incoming states having different azimuthal angles and further circularly and elliptically polarised incoming states in various variations.

BRIEF DESCRIPTION OF THE DRAWINGS

A brief description of the present invention is provided herein below with reference to the following diagrammatic drawings, in which.

DESCRIPTION OF THE PREFERRED EMBODIMENTS

Figure 1:
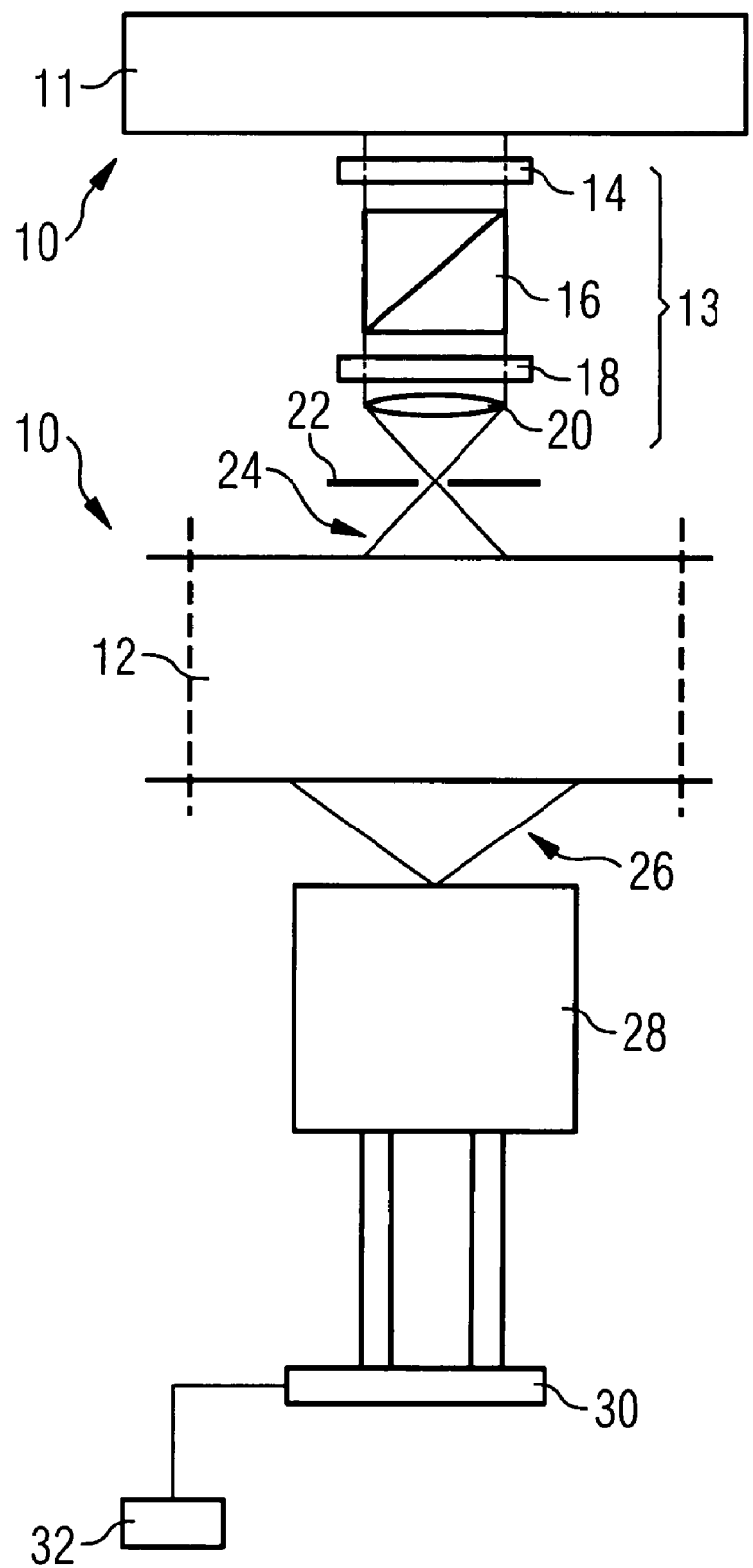
FIG. 1 is a schematic view of an exposure system for microlithography having projection optics and an assigned first embodiment of an apparatus for approximating an influence of the projection optics on the state of polarisation of optical radiation.

FIG. 1 is a schematic view showing a projection exposure system 10 for microlithography in conjunction with an assigned apparatus for approximating an influence of an optical system in form of a projection objective 12 of the exposure system 10 on the state of polarisation of optical radiation. The exposure system 10 comprises an illumination system 11 as the part of the system which supplies optical radiation, for example UV radiation in the wavelength region of about 248 nm or 193 nm and the projection objective 12 acting as an imaging subsystem of the exposure system. The projection objective 12 can be an optical imaging system having a comparatively high numerical aperture (NA). The design, which is so far conventional, is expanded by components of the assigned apparatus. The apparatus is specifically suitable for approximating the Jones matrix of the projection objective 12 in a spatially resolved fashion over the pupil range of the projection objective 12.

The apparatus includes means 13 for providing incoming optical radiation for the projection objective 12 in several incoming states of polarisation. These means 13 are arranged between the illumination system and the projection objective 12 and include, one behind another in the beam path, a diffusing screen 14, a rotatable polariser 16, a rotatable retarder 18 or compensator, and an aperture forming spot lens 20. Further, a coherence mask 22 in the form of a perforated mask or a so-called pinhole mask having one or more openings is arranged between the spot lens 20 and the projection objective 12.

The rotatable polariser 16 linearly polarises the optical radiation coming from the illumination system 11. The direction of the linear polarisation can be adjusted to any desired orientation by correspondingly rotating the polariser 16. The rotatable retarder 18 introduces a desired phase shift between the ordinary and the extraordinary portion of the optical wave entering. That means, both left-handed and right-handed circularly polarised light can be generated by the retarder 18. A combination of the rotatable polariser 16 and the rotatable retarder 18 therefore allows optical radiation of any Stokes vector to be provided to the projection objective 12.

The means 13 are configured for providing first incoming states of polarisation having predominantly linearly polarised radiation components and second incoming states of polarisation having predominantly circularly polarised radiation components, in particular at least two incoming states of oppositely oriented circular polarisation. For this purpose the rotatable retarder 18 can be provided in form of a λ/4-retarder, which is rotatable independently from the rotatable polariser 16. The orientation of the main axis of the retarder 18 is adjusted to azimuth angles of +45° and −45° with respect to the orientation of the polariser 16 in order to generate the circularly polarised radiation states. In order to generate the linear polarisation states the compensator 18 is oriented the same way as the polariser 16.

Alternatively, a fixed polariser can be used in combination with a λ/4-compensator oriented at azimuth angles of +45° and −45° with respect to the polarisation direction of the polariser for providing the circularly polarised radiation states. This arrangement of a fixed polariser and the correspondingly orientated λ/4-compensator can be moved into the optical path by lateral displacement.

The diffusing screen 14 is of a sufficiently strongly scattering design to provide spatially incoherent radiation. The coherence mask 22 is arranged in a focal plane of the spot lens 20, which is illuminated homogeneously to a very large extent and simultaneously forms the object plane of the projection objective 12. This yields a point light source, which is spatially as incoherent as possible in the object plane. The incoming optical radiation 24 provided therewith is directed onto the projection objective 12, from which it emerges as outgoing optical radiation 26. Subsequently the outgoing optical radiation 26 enters a shearing interferometer 28, to which a CCD detector 30 is connected. A suitably designed evaluation unit 32 is coupled to the CCD detector 30.

The shearing interferometer 28 is of a conventional design per se, for example as described in DE 101 09 929 A1 and the prior German patent application 102 17 242, to which reference can be made for further details. Required control and evaluation processes are implemented in the evaluation unit 32 as will become evident to the person skilled in the art from the following description of the associated process steps for evaluating the outgoing optical radiation 26.

In order to approximate an influence of the projection objective 12 on the state of polarisation of optical radiation the retardation R, its main axis .alpha., the transmission t, the linear dichroism d and the main axis of the linear dichroism β of the projection objective 12 are determined in a first measurement stage. For that purpose the incoming optical radiation 24 is provided by the means 13 in the above mentioned several first incoming states having predominantly linearly polarised radiation components. In a second measurement stage the rotation Rz and the circular dichroism dz are determined from the second incoming states having predominantly circularly polarised radiation components also provided by the means 13. From these parameters the evaluation unit 32 reconstructs an approximated Jones matrix of the projection objective 12.

The respective Polarisation matrix P of each of the first incoming states of the predominantly linearly polarised radiation and of each of the second incoming states of the predominantly circularly polarised radiation does not have to describe a completely polarised state. It can rather describe an arbitrary mix of linear, circular and non-polarised components. The repective degree of linear polarisation $\gamma_{lin}$ and the degree of circular polarisation $\gamma_{circ}$ can be obtained from the Polarisation matrix P as follows:

$$\gamma_{lin} = \frac{\sqrt{(P_{xx} - P_{yy})^2 + (P_{xy} + P_{yx})^2}}{P_{xx} + P_{yy}} \quad (1)$$

$$\gamma_{circ} = \frac{|P_{xy} - P_{yx}|}{P_{xx} + P_{yy}} \quad (2)$$

With this calculus it is possible to include the non-ideal effect of polarising optical elements into the evaluation of the outgoing optical radiation emerging from the projection objective 12. For the sake of measurement accuracy it is desirable if the first incoming states of polarisation used for determining the linear polarisation properties are provided with an as high as possible degree of linear polarisation. Accordingly, the second incoming states for determining the circular polarisation properties should be provided with an as high as possible degree of circular polarisation.

As mentioned above, in a first measurement stage the retardation R and the linear dichroism d of the projection objective 12 are determined. For this purpose a wave front phase distribution and an intensity distribution of the outgoing optical radiation emerging from the projection objective 12 with respect to the first incoming states of the predominantly linearly polarised radiation is determined using the shearing interferometer 28. For that purpose the first incoming states are provided with the azimuth angle φ of the respective polarisation direction being adjusted to at least three different orientations. Specifically the predominant polarisation direction of the linearly polarised radiation components of the first incoming polarisation states is varied by rotating the azimuth angle φ of its respective predominant polarisation direction in the range of 0°≦φ<180° in at least two steps. Preferably these steps are equal. That means, the azimuth angle φ of the predominant polarisation direction can for example be consecutively adjusted to 0°, 60° and 120°.

The intensity I of a respective interferogram created by the shearing interferometer 28 for a respective incoming state of polarisation, represented by the polarisation matrix P, is described by the following equation:

$$I = \text{trace } |(T+T_\Delta)P(T+T_\Delta)^+| = I_T + I_{T\Delta} + 2Re\{\text{trace}[TPT_\Delta^+]\} \quad (3)$$

Herein T is the pupil resolved Jones matrix of the projection objective and $T_\Delta$ is the corresponding Jones matrix at a pupil location shifted by a shearing distance. The plus sign in superscript denotes the complex conjugate of the respective matrix it refers to. $I_T$ and $I_{T\Delta}$ denote the respective intensity terms of two interfering partial optical waves of the shearing interferometer and the term (2 Re {trace $[TPT_\Delta^+]$}) denotes the interference term of the two interfering partial optical waves.

The polarisation matrix P which can also be referred to as coherence matrix is defined as the temporal average of the dyadic product of the corresponding electrical field E=[Ex, Ey] with itself as follows:

$$P = \langle E \circ E \rangle = \begin{Bmatrix} \langle E_x E_x^* \rangle & \langle E_x E_y^* \rangle \\ \langle E_y E_x^* \rangle & \langle E_y E_y^* \rangle \end{Bmatrix} \quad (4)$$

The star sign in superscript denotes the complex conjugate of the variable it refers to and the brackets < > denote to temporal averaging. For each of the incoming states of polarisation the phase distribution is measured by applying a so-called phase shifting technique. This is done by altering the phase of the sheared partial wave created in the shearing interferometer for a given incoming state of polarisation and measuring the respective resulting interferograms. Therefrom the complex argument (trace $[TPT_\Delta^+]$) of the last term in equation (3) can be determined. Therefrom the polarisation dependent differential phase term $\Delta\Phi_{pol}$ of the respective outgoing radiation can be calculated as follows:

$$\Delta\Phi_{pol} = \text{arg}(\text{trace } [TPT_\Delta^+]) \quad (5)$$

Further, the polarisation dependent intensity distribution $A_{pol}$, is obtained as follows:

$$A_{pol} = \text{abs}(\text{trace}[TPT_\Delta^+]) \quad (6)$$

Using the shearing interferometer a differential phase term ΔΦ of the outgoing optical radiation can be determined. As this is a differential dimension it has to be determined both for a shearing both in the x- and the y-direction. A desired polarisation dependent phase distribution $\Phi_{pol}$ is subsequently calculated from the two differential areas by integration using a suitable two-dimensional reconstruction algorithm. Accordingly, the phase distribution $\Phi_{pol}$ is determined over the pupil of the projection objective 12 except an offset value, which is constant over the whole pupil.

The intensity distribution $A_{pol}$ over the pupil of the projection objective 12 is only in a higher order subject to the shearing interferometer principle and can therefore be directly determined from the constant light portion of the phase shifted interferograms.

The phase distribution $\Phi_{pol}$ over the pupil and the intensity distribution $A_{pol}$ over the pupil is measured as described above for each of the first incoming states of predominantly linearly polarised radiation of different azimuth angles $\phi_n$, where $\phi_n$ are N values which propagate in equidistant steps from $\phi_1 > 0$ to $\phi_N = 360°$. A practical measure could be to perform the above described measurement only in equidistant steps $\phi_1 > 0$ to $\phi_{N/2} = 180°$ and to insert identical measured values for the angles $\phi_{N/2+1} > 180°$ to $\phi_N = 360°$, as the linear state of polarisation is invariant under rotation of $180°$.

Therefrom a phase distribution $\Phi_{pol}(\phi)$ and an intensity distribution $A_{pol}(\phi)$ as a function of the azimuth angle $\phi$ are obtained. These variables are then converted via Fourier Transform, which yields the coefficients of the respective complex harmonics a(n) and b(n) at each pupil location, as shown in the following:

$$a(n) = FT[\Phi_{pol}(\phi)] \quad (7)$$

$$b(n) = FT[A_{pol}(\phi)] \quad (8)$$

Practically, a fast fourier transform algorithm (FFT) can be applied in order to determine a(n) and b(n). In the above equations n denotes the respective order of the corresponding complex harmonic a(n) and b(n), respectively. From the first harmonic a(1) of the phase distribution $\Phi_{pol}(\phi)$ the retardation R of the projection objective 12 and the orientation $\alpha$ of its main axis can be determined as follows:

$$R = \frac{4}{N \cdot \gamma_{lin}} \text{abs}[a(1)] \quad (9)$$

$$\alpha = \frac{1}{2} \arg[a(1)] \quad (10)$$

Further, the transmission t, the linear dichroism d and the orientation of its main axis $\beta$ of the projection objective 12 is determined from the 0-th and the first harmonic b(0) and b(1) of the intensity distribution $A_{pol}(\phi)$ as follows:

$$t = \text{abs}[b(0)] \quad (11)$$

$$d = \frac{2}{t\gamma_{lin}} \text{abs}[b(1)] \quad (12)$$

$$\beta = \frac{1}{2} \arg[b(1)] \quad (13)$$

The factor ½ in the equations (10) and (13) represents the two-fold symmetry of the entire polarisation revolution. For determining the transmission t according to equation (11) the measurement apparatus has to be calibrated without the projection objective 12 to obtain a constant intensity value of 1.

As mentioned above, in a second measurement stage the rotation Rz and the circular dichroism dz are determined from the second incoming states of polarisation. The second incoming states include an incoming state of predominantly left-handed circularly polarised light and an incoming state of predominantly right-handed circularly polarised light and are provided one after the other by the means 13 including the rotatable retarder 18. As the rotation Rz of an optical system can also be interpreted as a retardation between left-handed circularly and right-handed circularly polarised light waves, it is possible to determine the rotation Rz by means of wave front measurement of two incoming states of oppositely oriented circular polarisations.

The differential phase term $\Delta\Phi_{pol}$ over the pupil is measured by means of the shearing interferometer 28 using the phase shifting technique described above for the left and the right handed circularly oriented polarisation states. Therefrom a phase distribution $\Phi_{pol}(lz)$ for the left-handed polarised incoming state and a phase distribution $\Phi_{pol}(rz)$ for the right-handed polarised incoming state are determined. As a next step the rotation Rz of the projection objective 12 is calculated as follows:

$$Rz = \frac{1}{2\gamma_{circ}} [\Phi_{pol}(lz) - \Phi_{pol}(rz)] \quad (14)$$

Further, the circular dichroism dz is calculated from the intensity distribution $A_{pol}(lz)$ for the left-handed circularly polarised light and the intensity distribution $A_{pol}(rz)$ for the right-handed circularly polarised incoming state as follows:

$$dz = \frac{A_{pol}(lz) - A_{pol}(rz)}{\gamma_{circ}[A_{pol}(lz) + A_{pol}(rz)]} \quad (15)$$

From the above determined parameters, namely the retardation R, the orientation of its main axis $\alpha$, the transmission t, the linear dichroism d, the orientation $\beta$ of its main axes, the rotation Rz and the circular dichroism dz an approximated Jones matrix of the projection objective 12 is calculated as described in the following.

Generally an approximated Jones matrix T can be reconstructed by use of the Jones matrix equivalence theorems laid out by R. Baracat, "Jones matrix equivalence theorems for polarisation theory", Eur. J. Phys. 19 (1998), 209-216, to which reference can be made for further details. According to these theorems any Jones matrix T can be decomposed as follows:

$$T = T_R(\alpha_1) T_{RP}(\alpha_2, \beta_1) T_P(\sigma_1, \sigma_2) T_{RP}(-\alpha_3, \beta_2) T_R(-\alpha_4) \quad (16)$$

Herein $T_R(\alpha_1)$ is the rotation matrix, which describes a rotation around the propagation axis by the angle $\alpha_1$. $T_{RP}(\alpha_2, \beta_1)$ the Jones matrix of an elementary retarder with the retardation $\alpha_2$ and the orientation $\beta_1$ of its fast main axis. $T_P(\sigma_1, \sigma_2)$ is the Jones matrix of a partial polariser in the main axes system having a larger transmission amplitude $\sigma_1$, and a smaller transmission amplitude $\sigma_2$. Not all variables of the above equation (16) can be determined by the above described method, including for example the distribution of the total retardation on the two elementary retarders $T_{RP}(\alpha_2, \beta_1)$ and $T_{RP}(-\alpha_3, \beta_2)$. However, in the Jones matrices measured by the method according to the invention, the inherent polariser $T_P(\sigma_1, \sigma_2)$ is sufficiently weak in order to combine the two elementary retarders $T_{RP}(\alpha_2, \beta_1)$ and $T_{RP}(-\alpha_3, \beta_2)$ to an effective retarder.

According to the invention, the total effective Jones matrix $T_{eff}$ can be calculated from the following equation $$T_{eff} = T_{lin} T_{circ} \quad (17)$$

wherein $$T_{lin} = T_{RP}(\alpha, R) T_R(\beta) T_P(\sigma_1, \sigma_2) T_R(Rz-\beta) \tag{18}$$

and $$T_{circ} = T_{RP}(\pi/4, \pi/2) T_R(\pi/4) T_P(\sigma_{1z}, \sigma_{2Z}) T_R(-\pi/4) T_{RP}(-\pi/4, \pi/2) \tag{19}$$

$T_{lin}$ is a representation of a Jones matrix containing the contributions of the retardation R, the linear dichroism d and the rotation Rz, while $T_{circ}$ is a representation of an additional Jones matrix, which describes the circular dichroism dz.

Further, $\sigma_1$ and $\sigma_2$ contained in equation (18) are the main transmission amplitudes of the Jones matrix for the partial polariser and are determined from the measured transmission t and the measured linear dichroism d as follows:

$$\sigma_1 = \sqrt{t(1+d)} \tag{20}$$

$$\sigma_2 = \sqrt{t(1-d)} \tag{21}$$

In analogue fashion the circular main transmission amplitudes $\sigma_{1z}$ and $\sigma_{2z}$ contained in equation (19) are calculated from the measured circular dichroism dz as follows:

$$\sigma_{1z} = \sqrt{1+dz} \tag{22}$$

$$\sigma_{2z} = \sqrt{1-dz} \tag{23}$$

The above model is based on the assumption that optical radiation passes first through a circular polariser then through a linear polariser and after that through an effective retarder. In case the actual Jones matrix of the projection objective 12 deviates from this behaviour, a modelling error between the actual Jones matrix and the reconstructed effective Jones matrix occurs. This modelling error however is unavoidable for the described method, as only a summed up retarder can be measured. The matrix multiplications shown in equations (17) to (19) can also be made in an alternate sequence which can represent a better approximation for a particular Jones matrix of the projection objective 12.

In the Jones matrix $T_{eff}$ according to equation (17) an arbitrary phase standardisation is included. The global phase, however, is given by the 0-th harmonic a(0) according to equation (7) and a corresponding phase standardisation could be made without difficulty.

Figure 2:
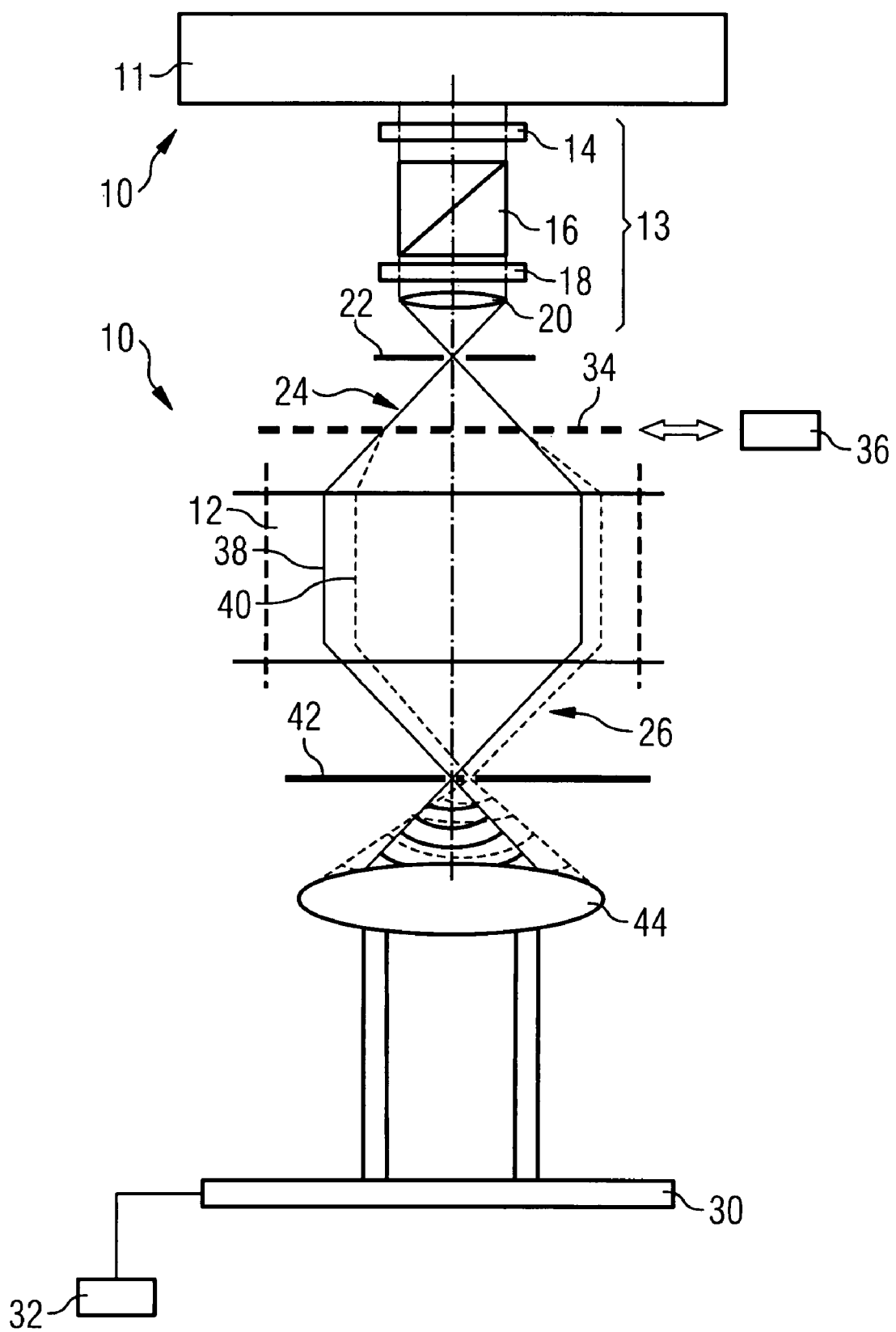
FIG. 2 is a schematic view of an exposure system for microlithography having projection optics and an assigned second embodiment of an apparatus for approximating an influence of the projection optics on the state of polarisation of optical radiation.

Instead of using the shearing interferometer 28 of the first embodiment shown in FIG. 1, a point-diffraction interferometer can be used, as contained in a second embodiment of the apparatus for approximating an influence of the projection objective 12 on the state of polarisation of optical radiation shown in FIG. 2. Elements of the embodiment shown in FIG. 2, which have the same function as corresponding elements in FIG. 1 are marked with the same reference numerals. Different from the first embodiment according to FIG. 1, in the second embodiment according to FIG. 2 use is made of a diffraction grating 34. By means of a diffraction effect the diffraction grating 34 splits the spherical wave produced by the coherence mask 22 into various component waves which are indicated by two partial waves 38 and 40. The two partial waves 38 and 40 traverse the projection objective 12 on similar trajectories and are subsequently focused onto pinholes of different size on a detector-side coherence mask 42. Because of the interference of the two partial waves 38 and 40 an interferogram of the entire projection objective 12 is produced, which is imaged onto the CCD detector 30 with the aid of beam shaping means 44.

The point-diffraction interferometer employed by the second embodiment according to FIG. 2 and the shearing interferometer 28 according to the first embodiment according to FIG. 1 are both common path interferometers, in which two partial optical waves creating the interferogram traverse the projection objective 12 along a common path. The use of such a common path interferometer is advantageous, as aberrations in the detection optics do not falsify the phase front measurement obtained therewith.

In the point-diffraction interferometer contained in the second embodiment according to FIG. 2 the wave front to be measured is brought into interference with a spherical wave generated by the pinhole of the coherence mask 42 in the focal plane of the projection objective 12 having a constant phase in a constant polarisation state. The corresponding phase distribution $\Phi_{pol}$ can be formulated in analogy to equation (5) as follows:

$$\Delta\Phi_{pol} = arg(\text{trace}[TPT_{Sph}^+]) \tag{24}$$

$T_{Sph}$ is a virtual Jones matrix, which defines the transformation of the polarisation state of the incoming light into the polarisation state of the spherical wave emerging from the pinhole of the coherence mask 22. The phase distribution $\Phi_{pol}$ is obtained by subsequent measurements of the interferograms generated by moving the diffraction grating 34 with the aid of an actuating unit 36, which causes a phase shifting corresponding to the phase shifting obtained by the phase shifting technique employed for the shearing interferometer 28.

The measurement method is otherwise identical with the measurement method described by the equations (1) to (23) with respect the shearing interferometer 28 except the following modification: the virtual Jones matrix $T_{Sph}$ is decomposed by means of singular value decomposition into the distinct product of a unitary matrix U, a diagonal matrix V and a further unitary matrix W.

$$T_{Sph} = UVW \tag{25}$$

Subsequently the unitary reference Jones matrix $T_{ref}$ is created as follows:

$$T_{ref} = UW \tag{26}$$

The reference Jones matrix $T_{ref}$ does not contain any amplitude distributions and is constant over all pupil locations due to the principle of the spherical wave. $T_{Sph}$ can be determined by means of an ellipsometric measurement at one pupil location or can be deducted from assumptions made on the projection objective 12 to be measured at one pupil location, for example at the location of the main beam.

Finally, the effective Jones matrix $T_{eff}$ determined according to the equations (1) to (23) is corrected by dividing the same by the reference Jones matrix $T_{ref}$. The resulting Jones matrix $T_{PDI}$ obtained by the measurement method using the point-diffraction interferometer according to FIG. 2 is determined as follows:

$$T_{PDI} = T_{eff} T_{ref}^{-1} \tag{27}$$

The present invention provides a method for approximating an influence of an optical system on the state of polarisation of optical radiation, in which method incoming optical radiation for the optical system is provided in several incoming states of polarisation, including linearly polarised and circularly polarised states. A phase distribution and an intensity distribution of a resulting outgoing optical radiation emerging from the optical system with respect to each of the incoming states of polarisation are measured and the influence of the optical system on the state of polarisation of optical radiation is approximated by calculating the retardation, the linear dichroism, the rotation and/or the circular dichroism of the optical system under test. The method according to the present invention allows approximation of an influence of an optical system on the state of polarisation with a high accuracy without the requirement of a polariser for measuring the outgoing optical radiation on the detector-side. Therefore, the cost of manufacturing a polariser for the detector side, which is generally subject to tight requirements due the need of providing sufficient transmission and extinction for large angles can be avoided. In particular for UV-wavelengths of λ=193 nm and λ=248 nm polarisers of sufficient quality for use as a detector-side polariser in an apparatus for determining the influence on the state of polarisation cannot be manufactured in a sufficient quality.

While the invention has been described with respect to a limited number of embodiments and applications, it will be appreciated that many variations, modifications and other applications of the invention may be made.

What is claimed is:

1. Method for approximating an influence of an optical system on the state of polarization of optical radiation comprising the steps of: providing incoming optical radiation for said optical system in several incoming states of polarization, directing said incoming optical radiation onto said optical system, measuring at least one characteristic of a resulting outgoing optical radiation emerging from said optical system with respect to each of said incoming states of polarization, approximating the influence of said optical system on the state of polarization of optical radiation by calculating at least one of the rotation and the circular dichroism of said optical system from said measured characteristics of said outgoing optical radiation, and calculating a Jones matrix of the optical system from the at least one of the rotation and the circular dichroism.

2. Method according to claim 1, wherein the at least one characteristic includes a phase distribution, wherein said measuring comprises using a common path interferometer, and wherein said approximating comprises evaluating said measured characteristics of said outgoing optical radiation.

3. Method according to claim 2, wherein said step of approximating the influence of said optical system on the state of polarization of optical radiation includes a reconstruction of an approximated Jones matrix of said optical system.

4. Method according to claim 2, wherein said incoming states of polarization are selected such that any arbitrary state of polarization can be formed by a linear combination of said incoming states of polarization.

5. Method according to claim 2, wherein said optical system comprises an optical imaging system having a given aperture, and said influence of said optical system on the state of polarization of optical radiation is determined with pupil resolution.

6. Method according to claim 2, wherein said incoming radiation is provided in at least one first incoming state having predominantly linearly polarized radiation components and at least one second incoming state having predominantly circularly polarized radiation components.

7. Method according to claim 6, wherein a predominant polarization direction of said linearly polarized radiation components of said at least one first incoming state is varied between at least three polarization directions obtained by rotating the azimuth angle of said predominant polarization direction in the range of $0° \leq \phi < 180°$ in equal steps.

8. Method according to claim 7, further comprising measuring a variation in a phase distribution and an intensity distribution of said measured outgoing optical radiation resulting from said variation of said predominant polarization direction, and determining the retardation and the linear dichroism of said optical system therefrom.

9. Method according to claim 6, wherein said at least one second incoming state comprises a first incoming circular polarization state of predominantly left-handed circularly polarized light and a second incoming circular polarization state of predominantly right-handed circularly polarized light.

10. Method according to claim 9, wherein the rotation and the circular dichroism of said outgoing system are determined from said measured characteristics of said outgoing optical radiation relating to said first and said second incoming circular polarization state.

11. Method according to claim 6, wherein the transmission of said optical system is determined from said measured characteristics of said outgoing optical radiation relating to at least one of said at least one first incoming state of polarization and said at least one second incoming state of polarization.

12. Method according to claim 2, wherein said incoming states of polarization are provided by varying the polarization state of said incoming optical radiation by means of at least one combination of a polarizer and a retarder, each of said at least one polarizer and said at least one retarder being independently adjustable in its respective spatial orientation.

13. Method according to claim 1, wherein measuring said at least one characteristic of said outgoing optical radiation includes the steps of measuring at least one of a phase distribution and an intensity distribution of said outgoing optical radiation with respect to each of said incoming states of polarization.

14. Method according to claim 13, wherein said step of measuring at least one of a phase distribution and an intensity distribution is carried out by means of an interferometer.

15. Method according to claim 13, wherein said step of approximating the influence of said optical system on the state of polarization of optical radiation includes the step of processing at least one of said measured phase distributions and said measured intensity distributions in a model function.

16. Method according to claim 1, wherein said step of approximating the influence of said optical system on the state of polarization of optical radiation includes a reconstruction of an approximated Jones matrix of said optical system.

17. Method according to claim 1, wherein said incoming states of polarization are selected such that any arbitrary state of polarization can be formed by a linear combination of said incoming states of polarization.

18. Method according to claim 1, wherein said optical system comprises an optical imaging system having a given aperture, and said influence of said optical system on the state of polarization of optical radiation is determined with pupil resolution.

19. Method according to claim 1, wherein said incoming radiation is provided in at least one first incoming state having predominantly linearly polarized radiation components and at least one second incoming state having predominantly circularly polarized radiation components.

20. Method according to claim 19, wherein a predominant polarization direction of said linearly polarized radiation components of said at least one first incoming state is varied between at least three polarization directions obtained by rotating the azimuth angle of said predominant polarization direction in the range of $0° \leq \phi < 180°$ in equal steps.

21. Method according to claim 20, further comprising measuring a variation in a phase distribution and an intensity distribution of said measured outgoing optical radiation resulting from said variation of said predominant polarization direction, and determining the retardation and the linear dichroism of said optical system therefrom.

22. Method according to claim 19, wherein said at least one second incoming state comprises a first incoming circular polarization state of predominantly left-handed circularly polarized light and a second incoming circular polarization state of predominantly right-handed circularly polarized light.

23. Method according to claim 22, wherein the rotation and the circular dichroism of said outgoing system are determined from said measured characteristics of said outgoing optical radiation relating to said first and said second incoming circular polarization state.

24. Method according to claim 19, wherein the transmission of said optical system is determined from said measured characteristics of said outgoing optical radiation relating to at least one of said at least one first incoming state of polarization and said at least one second incoming state of polarization.

25. Method according to claim 1, wherein said incoming states of polarization are provided by varying the polarization state of said incoming optical radiation by means of at least one combination of a polarizer and a retarder, each of said at least one polarizer and said at least one retarder being independently adjustable in its respective spatial orientation.

26. Method according to claim 1, wherein measuring said at least one characteristic of said outgoing optical radiation includes the steps of measuring at least one of a phase distribution and an intensity distribution of said outgoing optical radiation with respect to each of said incoming states of polarization.

27. Method according to claim 26, wherein said step of measuring at least one of a phase distribution and an intensity distribution is carried out by means of an interferometer.

28. Method according to claim 26, wherein said step of approximating the influence of said optical system on the state of polarization of optical radiation includes the step of processing at least one of said measured phase distributions and said measured intensity distributions in a model function.

29. Method for approximating an influence of an optical system on the state of polarization of optical radiation comprising the steps of:
  providing incoming optical radiation for said optical system in several incoming states of polarization including at least one incoming state having predominantly circularly polarized radiation components,
  directing said incoming optical radiation onto said optical system,
  measuring at least one characteristic of a resulting outgoing optical radiation emerging from said optical system with respect to each of said incoming states of polarization including measuring a phase distribution and an intensity distribution of the outgoing optical radiation with respect to each of the incoming states of radiation by means of an interferometer,
  wherein the phase distribution and the intensity distribution are respective distributions over at least portions of the exit pupil of the optical system,
  and approximating the influence of said optical system on the state of polarization of optical radiation by calculating at least one of the rotation and the circular dichroism of said optical system from said measured characteristics of said outgoing optical radiation.

* * * * *

UNITED STATES PATENT AND TRADEMARK OFFICE
CERTIFICATE OF CORRECTION

| | |
|---|---|
| PATENT NO. | : 7,924,436 B2 |
| APPLICATION NO. | : 11/703570 |
| DATED | : April 12, 2011 |
| INVENTOR(S) | : Markus Mengel et al. |

Page 1 of 1

It is certified that error appears in the above-identified patent and that said Letters Patent is hereby corrected as shown below:

In the Specifications:

Column 5, line 24: delete "an" and insert -- a --

Column 6, line 30: after "system" insert -- 11 --

Column 7, line 46: delete "repective" and insert -- respective --

Signed and Sealed this
Twenty-third Day of April, 2013

Teresa Stanek Rea
*Acting Director of the United States Patent and Trademark Office*